(12) United States Patent
Nikkhah et al.

(10) Patent No.: US 11,364,321 B2
(45) Date of Patent: Jun. 21, 2022

(54) NANO SCALE DECORATION OF SCAFFOLD-FREE MICROTISSUE USING FUNCTIONALISED GOLD NANOSTRUCTURES

(71) Applicants: Arizona Board of Regents on Behalf of Arizona State University, Scottsdale, AZ (US); The United States of America as Represented by The Department of Veterans Affairs, Washington, DC (US)

(72) Inventors: Mehdi Nikkhah, Scottsdale, AZ (US); Ali Navaei, Tempe, AZ (US); Raymond Migrino, Phoenix, AZ (US)

(73) Assignees: Arizona Board of Regents on Behalf of Arizona State University, Scottsdale, AZ (US); The United States of America as Represented by The Department of Veterans Affairs, Washington, DC (US)

(*) Notice: Subject to any disclaimer, the term of this patent is extended or adjusted under 35 U.S.C. 154(b) by 639 days.

(21) Appl. No.: 16/157,956

(22) Filed: Oct. 11, 2018

(65) Prior Publication Data
US 2019/0275203 A1    Sep. 12, 2019

Related U.S. Application Data

(60) Provisional application No. 62/571,056, filed on Oct. 11, 2017.

(51) Int. Cl.
*C12N 5/071*    (2010.01)
*A61L 27/38*    (2006.01)
(Continued)

(52) U.S. Cl.
CPC .......... *A61L 27/22* (2013.01); *A61L 27/047* (2013.01); *A61L 27/26* (2013.01);
(Continued)

(58) Field of Classification Search
CPC ...... A61L 27/22; A61L 27/26; A61L 27/3604; A61L 27/3821; A61L 27/3873; C12N 5/0656; C12N 5/0658; C12N 2501/165
See application file for complete search history.

(56) References Cited

U.S. PATENT DOCUMENTS

| | | |
|---|---|---|
| 4,612,302 A | 9/1986 | Szabo et al. |
| 4,684,620 A | 8/1987 | Hruby et al. |

(Continued)

FOREIGN PATENT DOCUMENTS

WO    2018208782 A1    11/2018

OTHER PUBLICATIONS

Gandaglia et al. "Cardiomyocytes in Vitro Adhesion is Actively Influenced by Biomimetic Synthetic Peptides for Cardiac Tissue Engineering" Tissue Engineering: Part A, vol. 18, No. 7 and 8, 2012 (Year: 2012).*

(Continued)

*Primary Examiner* — Marcia S Noble
*Assistant Examiner* — Lauren K Van Buren
(74) *Attorney, Agent, or Firm* — Viksnins Harris Padys Malen LLP

(57) ABSTRACT

A scaffold-free microtissue is disclosed that includes one or more gold nanostructures linked to a functional moiety, wherein the functional moiety is one or more vasculogenic peptides, one or more anti-inflammatory peptides, one or more antiapoptotic peptides, one or more antinecrotic peptides, one or more antioxidant peptides, one or more oligonucleotides, one or more lipid particles, one or more phospholipid particles, one or more liposomes, one or more (Continued)

nanoliposomes, one or more microRNAs, or one or more siRNAs. The scaffold-free microtissue further includes a plurality of cardiac myocytes or cardiac myoblasts, which are conjugated to the one or more gold nanostructures, wherein the plurality of cardiac myocytes or cardiac myoblasts are arranged in a cluster. The scaffold-free microtissue further includes a plurality of fibroblasts, wherein the fibroblasts are arranged in at least one layer of fibroblasts that substantially surrounds the cluster of gold-nanostructure-conjugated cardiac myocytes or gold-nanostructure-conjugated cardiac myoblasts.

15 Claims, 8 Drawing Sheets

Specification includes a Sequence Listing.

(51) Int. Cl.
A61L 27/22 (2006.01)
A61L 27/26 (2006.01)
A61L 27/36 (2006.01)
C12N 5/077 (2010.01)
A61L 27/04 (2006.01)
A61L 27/54 (2006.01)

(52) U.S. Cl.
CPC ....... *A61L 27/3604* (2013.01); *A61L 27/3804* (2013.01); *A61L 27/3821* (2013.01); *A61L 27/3826* (2013.01); *A61L 27/3873* (2013.01); *A61L 27/3886* (2013.01); *A61L 27/3895* (2013.01); *A61L 27/54* (2013.01); *C12N 5/0656* (2013.01); *C12N 5/0658* (2013.01); *A61L 2430/20* (2013.01); *C12N 2501/165* (2013.01)

(56) References Cited

U.S. PATENT DOCUMENTS

| | | | |
|---|---|---|---|
| 4,853,371 A | 8/1989 | Coy et al. | |
| 8,188,053 B2 | 5/2012 | Cumberbatch et al. | |
| 10,017,724 B2 | 7/2018 | Nikkhah et al. | |
| 10,265,439 B2 | 4/2019 | Nikkhah et al. | |
| 2015/0125952 A1* | 5/2015 | Kim | C12N 5/0658 435/366 |
| 2016/0106886 A1* | 4/2016 | Dvir | A61L 27/3826 435/402 |
| 2016/0361462 A1* | 12/2016 | Yim | B32B 27/306 |
| 2017/0067025 A1 | 3/2017 | Nikkhah et al. | |
| 2017/0143871 A1 | 5/2017 | Nikkhah et al. | |
| 2018/0052151 A1 | 2/2018 | Nikkhah et al. | |

OTHER PUBLICATIONS

Wang et al. "Efficient, dual-stimuli responsive cytosolic gene delivery using a RGD modified disulfide-linked polyethylenimine functionalized gold nanorod" Journal of Controlled REIease 196 (2014) 37-51. (Year: 2014).*
Navaei et al. "Gold nanorod-incoporated gelatin based conductive hydrogels for engineering cardiac tissue constructs" Acta Biomaterialia 41 (2016) 133-146. (Year: 2016).*
Van Meer "Membrane liipids: where they are and how they behave" Nat Rev Mol Cell Biol. Feb. 2008; 9(2): 112-124.*
Culman et al. "Antisense oligonucleotides in the study of central mechanisms of the cardiovascular regulation" Experimental Physiology (2000) 85. 6, 757-767.*
Daraee et al. "Application of liposomes in medicine and drug delivery Artificial Cells, Nanomedicine, and Biotechnology" 2016, 44: 381-391.*
Tan et al. "DNA, RNA, and Protein Extraction: The Past and the Present" Journal of Biomedicine and Biotechnology vol. 2009, 10 pages.*
Saini et al. "3D Cardiac Microtissues Encapsulated with the Co-Culture of Cardiomyocytes and Cardiac Fibroblasts" Adv. Healthcare Mater. 2015, 4, 1961-1971. (Year: 2015).*
Andersen, H , et al., "MicroRNAs as modulators and biomarkers of inflammatory and neuropathic pain conditions", Neurobiology of Disease 71, 159-168 (2014).
Boisguerin, P , et al., "Systemic delivery of BH4 anti-apoptotic peptide using CPPs prevents cardiac ischemia-reperfusion injuries in vivo", Journal of Controlled Release 156(2), 146-153 (2011).
Chen, H , et al., "Antioxidant Activity of Designed Peptides Based on the Antioxidative Peptide Isolated from Digests of a Soybean Protein", Journal of Agriculture and Food Chemistry 44(9), 2619-2623 (1996).
Cook, A , et al., "Characterization and development of RGD-peptide-modified poly(lactic acid-co-lysine) as an interactive, resorbable biomaterial", Journal of Biomedical Materials Research 35(4), 513-523 (1997).
Dvir, T , et al., "Nanowired three-dimensional cardiac patches", Nature Nanotechnology 6, 720-725 (2011).
Fleischer, S , et al., "Coiled fiber scaffolds embedded with gold nanoparticles improve the performance of engineered cardiac tissues", Nanoscale 6, 9410-9414 (2014).
Franco, D , et al., "Monosialoganglioside-Containing Nanoliposomes Restore Endothelial Function Impaired by AL Amyloidosis Light Chain Proteins", Journal of the American Heart Association 5(6), 10 pages (2016).
Keefe , et al., "Aptamers as therapeutics", Nat Rev Drug Discov 9, 537-550 (2010).
Kharaziha, M , et al., "Tough and flexible CNT-polymeric hybrid scaffolds for engineering cardiac constructs", Biomaterials 35(26), 7346-7354 (2014).
Kinnear, C , et al., "Aptamers as therapeutics", Nature Reviews Drug Discovery 9, 537-550 (2010).
Kumar, V , et al., "Highly Angiogenic Peptide Nanofibers", ACS Nano 9(1), 860-868 (2015).
Lebaron, R , et al., "Extracellular Matrix Cell Adhesion Peptides: Functional Applications in Orthopedic Materials", Tissue Engineering 6(2), 85-103 (2000).
Martinelli, V, et al., "Carbon Nanotubes Promote Growth and Spontaneous Electrical Activity in Cultured Cardiac Myocytes", Nano Lett 12, 1831-1838 (2012).
Park, J , et al., "Graphene Potentiates the Myocardial Repair Efficacy of Mesenchymal Stem Cells by Stimulating the Expression of Angiogenic Growth Factors and Gap Junction Protein", Advanced Functional Materials 25(17), 2590-2600 (2015).
Parthiban, S , et al., "Covalently immobilized VEGF-mimicking peptide with gelatin methacrylate enhances microvascularization of endothelial cells", Acta Biomaterialia 51, 330-340 (2017).
Paul, A, et al., "Injectable graphene oxide/DNAVEGF based hydrogel for vasculogenesis and cardiac repair", ACS Nano 8(8), 8050-8062 (2014).
Pierschbacher, M , et al., "Cell attachment activity of fibronectin can be duplicated by small synthetic fragments of the molecule", Nature 309, 30-33 (1984).
Pierschbacher, M , et al., "Variants of the cell recognition site of fibronectin that retain attachment promoting activity". Proceedings of the National Academy of Sciences of the United States of America 81(19), 5985-5988 (1984).
Pok, S , et al., "Biocompatible carbon nanotube-chitosan scaffold matching the electrical conductivity of the heart", ACS Nano 8(10), 9822-9832 (2014).
Richards, D , et al., "Nanowires and Electrical Stimulation Synergistically Improve Functions of hiPSC Cardiac Spheroids", Nano Letters 16(7), 4670-4678 (2016).
Shevach, M , et al., "Gold Nanoparticle-Decellularized Matrix Hybrids for Cardiac Tissue Engineering", Nano Letters 14(10), 5792-5796 (2014).
Shevach, M , et al., "Nanoengineering gold particle composite fibers for cardiac tissue engineering", J Mater Chem B 1(39), 5210-5217 (2013).

(56) References Cited

OTHER PUBLICATIONS

Shin, S., et al., "Carbon nanotube reinforced hybrid microgels as scaffold materials for cell encapsulation", ACS Nano 6(1), 362-372 (2012).

Shin, S., et al., "Carbon-Nanotube-Embedded Hydrogel Sheets for Engineering Cardiac Constructs and Bioactuators", ACS Nano 7(3), 2369-2380 (2013).

Tan, Y., et al., "Silicon Nanowire-Induced Maturation of Cardiomyocytes Derived from Human Induced Pluripotent Stem Cells", Nano Letters 15(5), 2765-2772 (2015).

You, J., et al., "Nanoengineering the heart: conductive scaffolds enhance connexin 43 expression", Nano Letters 11(9), 3643-3648 (2011).

Zhang, Z., et al., "Fast loading of PEG-SH on CTAB-protected gold nanorods", RSC Advances 4(34), 17760-17767 (2014).

Zhou, J., et al., "Engineering the heart: Evaluation of conductive nanomaterials for improving implant integration and cardiac function", Scientific Reports 4(art. No. 3733), 11 pages (2014).

* cited by examiner

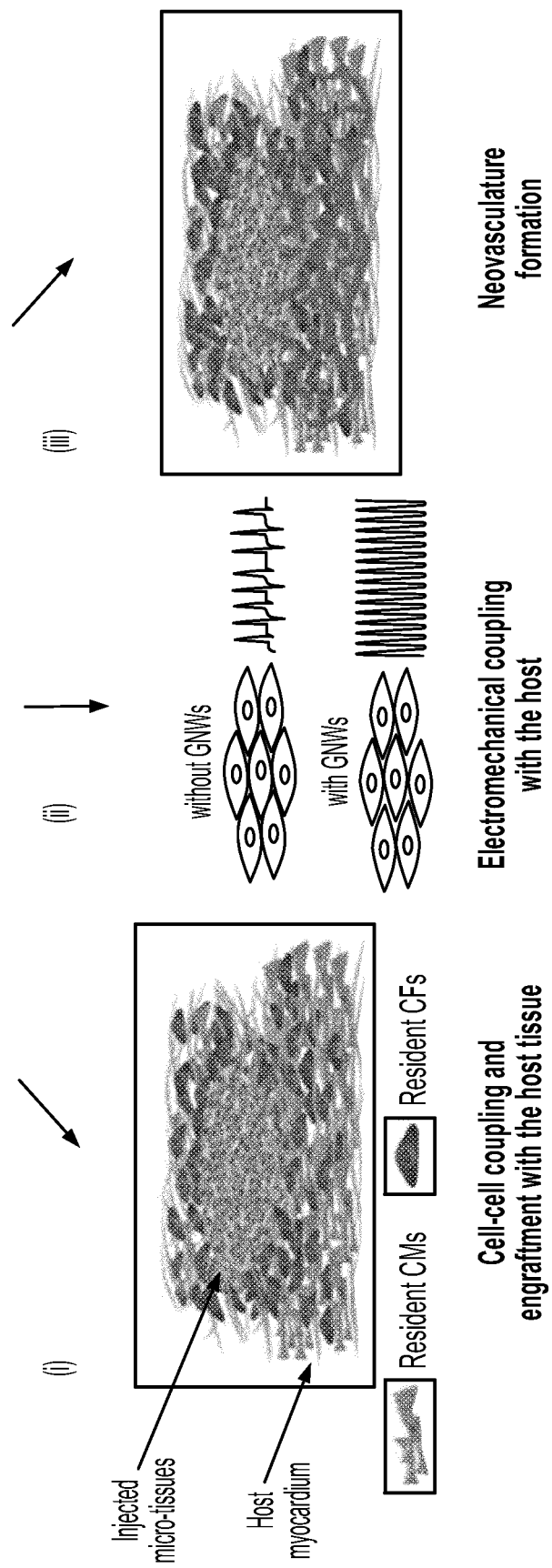

SEQUENCE LISTING

```
<160> NUMBER OF SEQ ID NOS: 6

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(1)
<223> OTHER INFORMATION: K(Ac)
<220> FEATURE:
<221> NAME/KEY: MISC_FEATURE
<222> LOCATION: (11)..(11)
<223> OTHER INFORMATION: K(Ac)
<220> FEATURE:
<221> NAME/KEY: MISC_FEATURE
<222> LOCATION: (13)..(13)
<223> OTHER INFORMATION: K(Ac)

<400> SEQUENCE: 1

Lys Leu Thr Trp Gln Glu Leu Tyr Gln Leu Lys Tyr Lys Gly Ile
1               5                   10                  15
```

```
<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Leu Thr Trp Gln Glu Leu Tyr Gln Leu Lys Tyr Lys Gly Ile
1               5                   10                  15

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Gly Glu Ala
1

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Arg Gly Asp Ser Pro
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Arg Gly Asp Tyr
1               5

<210> SEQ ID NO 6
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Lys Ser Leu Ser Leu Ser Leu Arg Gly Ser Leu Ser Leu Ser Leu Lys
1               5                   10                  15

Gly Lys Leu Thr Trp Gln Glu Leu Tyr Gln Leu Lys Tyr Lys Gly Ile
                20                  25                  30
```

NANO SCALE DECORATION OF SCAFFOLD-FREE MICROTISSUE USING FUNCTIONALISED GOLD NANOSTRUCTURES

CROSS-REFERENCE TO RELATED APPLICATION(S)

This application claims priority to U.S. Provisional Application No. 62/571,056 filed on Oct. 11, 2017. The entire content of the application referenced above is hereby incorporated by reference herein.

SEQUENCE LISTING

The instant application contains a Sequence Listing which has been filed electronically in ASCII format and is hereby incorporated by reference in its entirety. Said ASCII copy, created on May 29, 2019, is named 17555 057US1 SL.txt and is 2,203 bytes in size.

BACKGROUND

Approximately 6.5 million people in the U.S. are diagnosed with heart failure, with 4134 patients (May 2016) on a waiting list to receive a heart transplant. Cardiovascular diseases, including myocardial infarction (MI), remain a leading cause of mortality and morbidity worldwide, accounting for over 40% of all human death. MI leads to loss of cardiomyocytes (CMs), which have limited self-regenerative capacity, leading to impaired contractility, abnormal stress distribution throughout the heart, adverse global remodeling and ultimately heart failure. Heart transplantation or implantation of mechanical left ventricular assist device are treatment options of last resort, but are limited by inadequate organ donors and potential complications of the surgical procedures. For the vast majority of heart failure patients, treatment is limited to pharmacologic therapy to optimize the function of remaining CMs and slow the adverse cardiac remodeling. Those skilled in the art will appreciate that cardiomyocytes and cardiac myocytes are different terms for the same types of cells.

Over the last decade, alternative approaches were developed for myocardial replacement therapy (MRT), but results have so far been disappointing. These strategies comprised of cell-based transplantation, injectable biomaterials (i.e. cell-laden or acellular) or engineered tissue constructs. The common goal of these approaches is to restore native-like functionalities (i.e. enhanced contractility) while maintaining structural integrity of the myocardium.

The clinical use of cell-based MRT has been hampered by the high rate of cell loss and poor cell-cell coupling and engraftment with host myocardium. Cell-based MRT involves local injection of stem/progenitor or adult cells into infarcted myocardium to augment existing pool of CMs and initiate an endogenous regeneration process. This approach has many potential advantages including use of less invasive procedures, lack of reliance on availability of donor hearts and use of patient's own cells to obviate immune reactions. Cell-based MRT approaches include of direct injection of adult cells (e.g. skeletal myoblasts, mesenchymal), cardiac stem/progenitor cells (e.g. C-kit27 cardiac side population, sca, Islet, cardiosphere) as well as human pluripotent stem cells (hiPSCs). Current cell-based MRT approaches, however, are hampered by poor (~50%) cell retention, inadequate cell-cell coupling and poor engraftment with the host myocardium, with only 10% survival of injected cells. The shortcomings of cell-based MRT generated interest in embedding the desired cells into scaffolding matrices to serve as "tissue engineered cardiac patches" or "injectable cell-laden biomaterials" (i.e. scaffold-based approaches) that could be locally applied to the injured zone. Various approaches utilized natural (e.g. alginate, fibrin, collagen, extracellular matrices) or synthetic materials (i.e. PNIPAAm, self-assembling peptides) for injection or implantation (i.e. patch) of cells into the infarcted region. However, in vivo pre-clinical studies of cell-embedded biomaterials have so far demonstrated inconsistent outcomes due to lack of electromechanical integration (i.e. synchronous contraction) of the tissues with the host myocardium, raising the potential risk of arrhythmias, as well as poor vascularization. Furthermore, implantation of cell-embedded patches can potentially cause immune rejection or foreign body reactions while requiring a highly invasive approach (i.e. open-heart surgery) to implant the tissues.

Regenerative Medicine and tissue engineering strategies offer promising avenues to address the current limitations in organ transplantation in general, and cardiac repair in particular. Native ventricular myocardium consists of CMs coupled with electrically conductive purkinje fibers and mechanically robust extracellular matrix (ECM). This unique architecture exhibits tightly packed and aligned (i.e. anisotropic) cellular constructs. Following injury, replacement of infarcted myocardium would require proper scaffolding biomaterials and cell sources to mimic the structural architecture of native myocardium. Although substantial progress has been made in the synthesis of new biomaterials to replace injured cardiac tissue using natural or synthetic polymers (collagen, elastin, silk, gelatin, etc), unfortunately, the electrical properties of these hydrogels do not come close to the properties of the native myocardium. Inadequate cell adhesion sites and electrically insulated structure of conventional hydrogels lead to poor tissue-level functionalities, lack of integration with the host myocardium, and ultimately failure of the tissue engineered constructs.

To date, several studies have demonstrated that employing electrically conductive nanomaterials enables addressing the shortcomings of conventional hydrogel-based scaffolds with respect to their electrical conductivity. Carbon nanotubes (CNT) have been among well respected conductive nanomaterials for cardiac tissue engineering. CNTs-embedded scaffolds have particularly demonstrated enhanced electrical properties that facilitated electrical signal propagation and cell-cell coupling. While incorporation of CNTs results in superior properties, several controversial cytotoxicity issues have raised numerous concerns for their use in clinical applications.

Due to these critical shortcomings, there is still an unmet need to develop treatment strategies for long-term regeneration of injured myocardium.

SUMMARY

A scaffold-free microtissue comprising gold nanostructures within the microtissue.

In one or more embodiments, the microtissue comprises cardiac myocytes, endothelial cells, pluripotent stem cells, myoblasts, or fibroblasts.

In one or more embodiments, the gold nanostructures are 1D gold nanostructures.

In one or more embodiments, the 1D gold nanostructures are wires, rods, or spheres.

In one or more embodiments, the gold nanostructures include 2D gold nanostructures.

In one or more embodiments, the 2D gold nanostructures are nano-plates.

In one or more embodiments, one or more gold nanostructures are linked to a cell adhesion moiety.

In one or more embodiments, the cell adhesion moiety is a peptide.

A cardiac microtissue comprising nanoscale decoration of cardiac cells including gold nanostructures within the microtissue.

In one or more embodiments, the microtissue is scaffold free.

In one or more embodiments, the gold nanostructures are functionalized using RGD cell adhesion motifs.

In one or more embodiments, the gold nanostructures are capped with polyethylene glycol bi-linker.

In one or more embodiments, the microtissue is spheroid based.

In one or more embodiments, the gold nanostructures are conjugated with vasculogenic peptides.

In one or more embodiments, the microtissue further includes functionalized cardiomyocytes and cardiac fibroblasts within the gold nanostructures.

In one or more embodiments, an electrically conductive composition comprising cardiac micro-tissue and gold nanostructures is described herein.

In one or more embodiments, a method for regeneration or repair of infarcted myocardium in an animal comprises injecting a composition as described above.

In one or more embodiments, the composition is injected within the infarcted region of myocardium of the animal.

In one or more embodiments, an electrically conductive composition as described above for use in medical therapy.

In one or more embodiments, an electrically conductive composition as described above for regeneration or repair of infarcted myocardium.

In one or more embodiments, the use of an electrically conductive composition as described above to prepare a medicament for regeneration or repair of infarcted myocardium.

Consistent with the disclosed embodiments, a scaffold-free microtissue is disclosed. The scaffold-free microtissue comprises one or more gold nanostructures linked to a functional moiety, wherein the functional moiety is one or more vasculogenic peptides, one or more anti-inflammatory peptides, one or more antiapoptotic peptides, one or more antinecrotic peptides, one or more antioxidant peptides, one or more oligonucleotides, one or more lipid particles, one or more phospholipid particles, one or more liposomes, one or more nanoliposomes, one or more microRNAs, or one or more siRNAs. The scaffold-free microtissue further comprises a plurality of cardiac myocytes or cardiac myoblasts, wherein the cardiac myocytes or cardiac myoblasts are conjugated to the one or more gold nanostructures, wherein the plurality of cardiac myocytes or cardiac myoblasts are arranged in a cluster. The scaffold-free microtissue further comprises a plurality of fibroblasts, wherein the fibroblasts are arranged in at least one layer of fibroblasts that substantially surrounds the cluster of gold-nanostructure-conjugated cardiac myocytes or gold-nanostructure-conjugated cardiac myoblasts.

Consistent with the disclosed embodiments, a method for regeneration or repair of an infarcted myocardium including an infarcted region in an animal comprises injecting a scaffold-free microtissue into the animal.

BRIEF DESCRIPTION OF THE DRAWINGS

FIG. 1D illustrates cell-cell coupling and engraftment with host tissue, in accordance with one or more embodiments.

FIG. 1E illustrates enhanced electromechanical integration (i.e. synchronous contraction) of the micro-tissues with the host myocardium due to high conductivity properties of GNWs.

FIG. 1F illustrates neovascular formation within the micro-tissues due to conjugation of VEGF-mimetic vasculogenic peptide to GNWs, in accordance with one or more embodiments.

DETAILED DESCRIPTION

Figures 1A, 1B, 1C:
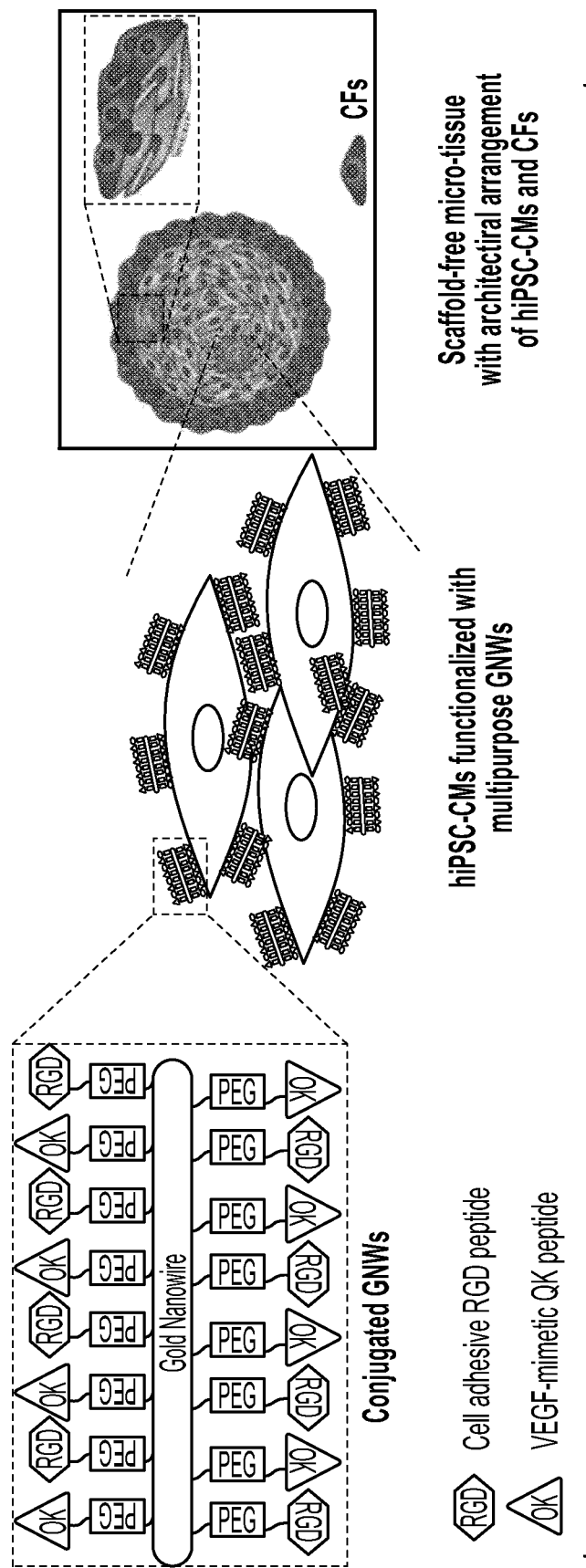
FIG. 1A illustrates conjugated, scaffold-free cardiac micro tissues using electrically conductive, cell adhesion-promoting and vasculogenic gold nanowires (GNWs), in accordance with one or more embodiments.
FIG. 1B illustrates hiPSC-CMs functionalized with multipurpose GNWs, in accordance with one or more embodiments.
FIG. 1C illustrates scaffold-free micro-tissue with architectural arrangement of hiPSC-CMs and cardiac fibroblasts (CFs), in accordance with one or more embodiments.
Figures 2A, 2B, 2C, 2D, 2E:
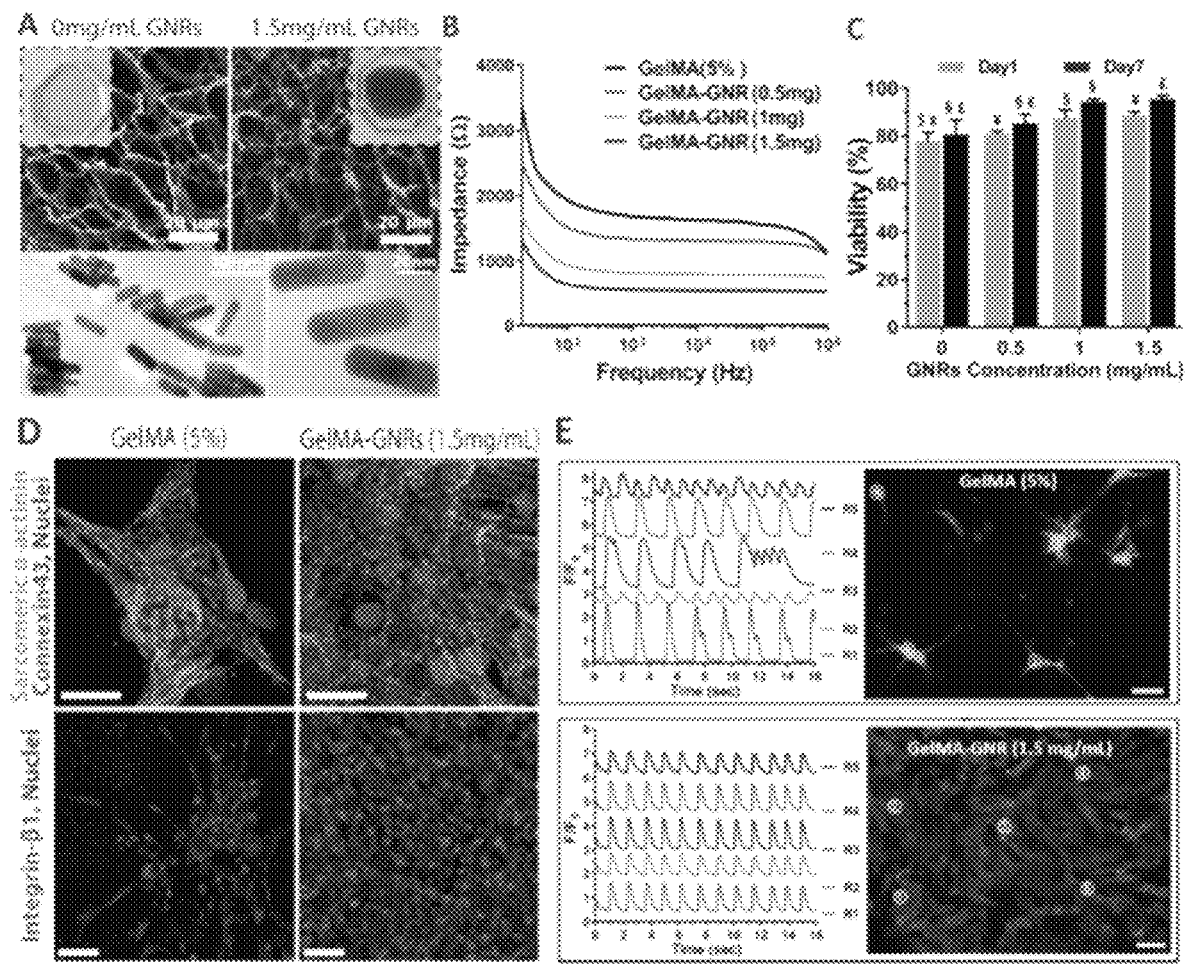
FIG. 2A illustrates synthesized GNRs incorporated within gelatin-based hydrogels (GelMA-GNRs) with improved electrical, structural properties, in accordance with one or more embodiments.
FIG. 2B illustrates the electrical properties of GNRs incorporated within gelatin-based hydrogels (GelMA-GNRs), in accordance with one or more embodiments.
FIG. 2C illustrates GNR concentration v. viability of neonatal rat CMs seeded on GelMA-GNWs tissues, in accordance with one or more embodiments.
FIG. 2D illustrates homogeneous distribution of cardiac specific markers (sarcomeric α-actinin) and Connexin43 (CX43) gap junction protein along with increased cell binding to the matrix (integrin β-1) confirmed the formation of an integrated tissue layer, in accordance with one or more embodiments.
FIG. 2E illustrates conductive GNRs embedded gelatin scaffolds significantly supported synchronous tissue-level contractility and calcium transient of CMs, in accordance with one or more embodiments.

In one or more embodiments, Gold Nanostructures and microengineering technology are used to develop an injectable electrically conductive spheroid-based micro-tissue, embedded with gold nanowires or nanorods, for functional regeneration of infarcted myocardium.

Electrically conductive and highly functional cardiac micro-tissues nano-engineered with gold nanowires for regeneration and repair of infarcted myocardium. The developed micro-tissues can be injected (or implanted) within the infarcted region of myocardium to restore the tissue function loss and prevent heart failure (See FIG. 5A-5G). The electrically conductive cardiac micro-tissues provide a desirable microenvironment to enhance the functionalities of cardiac cells and to better integrate to the native heart.

Biocompatible and functionalized gold nanowires (GNWs) are synthesized to decorate the intercellular microenvironment of the cardiac microtissues.

In one or more embodiments, the GNWs were capped with polyethylene glycol bi-linker (COOH-PEG-SH) and functionalized using RGD cell adhesion motifs to 1) increase the biocompatibility of the conventional GNWs capped with toxic surfactant (Cetrimonium bromide, CTAB), 2) induce high negative surface charge to decrease the intracellular uptake, and 3) increase the GNW-cell interaction to enhance the spheroid structural integrity.

Spheroid-based cardiac micro-tissues, with well defined geometrical features and mix functionalized GNWs with the micro-tissues are used to develop the final electrically conductive and injectable spheroid based cellular clusters.

The procedure is minimally invasive, given that our injectable and electrically conductive micro-tissues can be directly delivered via catheter to the infarcted zone of myocardium (i.e., chest cavity not opened). In one or more embodiments, the micro-tissues can be delivered via a minimally invasive surgical catheter based delivery. The developed tissues could be used for in vivo testing in both small and large animal models.

The preparation and functionalization of the GNWs can be conducted in a number of different manners. In one or more examples, preparation and functionalization of GNWs: and GNW-CTAB with average aspect ratio of 21 (~1.1 μm length & ~55 nm diameter) was synthesized. GNWs capped with SH-PEG-COOH (GNW-COOH) was synthesized via a customized 2-step exchange procedure including primary PEGylation in Tris buffer (pH 3, 24 hr) followed by post-PEGylation in ethanol (20%, 24 hr). RGD functionalized GNWs (GNW-RGD) was synthesized using GNW-COOH and RGD peptide based on EDC/NHS protocol. Transmission electron microscopy, Raman spectroscopy and dynamic light scattering were used to characterize the produced GNWs (-CTAB, —COOH and -RGD).

Generation of cardiac micro-tissues: polydimethylsiloxane (PDMS) or Agarose concave microwells are used based on well-established protocols and our preliminary studies to engineer micro-tissues. Briefly, a micro-engineered master composed of an array of 20×20 concave microwells in the range of 100-300 μm diameter and 150 μm in spacing will be purchased or fabricated using SU-8 photoresist and soft lithography technique. Subsequently, a 10:1 mixture of elastomer and curing agent will be poured on PDMS master and racked out using a glass slide by applying light pressure. Surface tension will allow formation of meniscus on cylindrical microwells of PDMS master leading to formation of concave microwells. Cardiac cells mixed with functionalized GNWs having concentrations of 1, 10 and 50 micro-grams/ml will be seeded on microwells at a density of $10-15 \times 10^{\wedge}6$ cells/ml of cardiac media. Passive cell seeding is expected to lead to formation of cellular clusters within each microwell. Upon cell seeding, microwells will be placed inside 37° C. for 7 days to form micro-tissues.

In one or more embodiments, a unique and integrated strategy is proposed to develop next generation of MRT based on nanoengineering of scaffold-free cardiac microtissues using electrically conductive, cell adhesion-promoting and vasculogenic gold nanowires (GNWs) (FIG. 1A). Cardiomyocytes (CMs), functionalized on the cell surface, with GNWs that are conjugated with cell adhesion-promoting and vasculogenic or other peptides (FIG. 1B), as the primary building blocks of the micro-tissues. Microscale technologies will be used to generate the scaffold-free tissues comprised of co-culture of functionalized CMs and cardiac fibroblast (CFs), with specific architectural arrangement (FIG. 1C). In certain embodiments, the architectural arrangement may include a plurality of CFs arranged in at least one layer of fibroblasts that surrounds, encompasses, encircles, envelops, or encapsulates a cluster of CMs (e.g., functionalized CMs). In other embodiments, other architectural arrangements may be utilized. Since, gold nanomaterials-embedded scaffolds improve functional outcome in MRT, direct functionalization of CMs with multipurpose GNWs will allow scaffold-free MRT constructs that will lead to: a) establishment of mature cell-cell coupling due to GNWs that are conjugated with adhesion-promoting RGD peptide (FIG. 1D); b) enhanced electromechanical integration (i.e. synchronous contraction) of the micro-tissues with the host myocardium due to high conductivity properties of GNWs (FIG. 1E); and c) promotion of neovascular formation within and from the host towards the micro-tissues due to conjugation of VEGF-mimetic peptide to GNWs (FIG. 1F). Addition of CFs, with specific architectural arrangement (i.e. within the outer layer of microtissues), will further enhance engraftment of the micro-tissues with the host while simultaneously promoting a native like endogenous niche through ECM production and paracrine CM-CF signaling. The proposed strategy produces injectable micro-tissues for intramyocardial delivery via minimally invasive catheter-based approach.

In some embodiments, scaffold-free, electrically conductive and vasculogenic cardiac micro-tissue include hiPSCs-CMs and CFs. In some embodiments, in vitro maturity and functionalities of micro-tissues including GNWs conjugated with RGD and VEGF-mimetic QK peptides is assessed. In some embodiments, scaffold-free cardiac micro-tissues including GNW-functionalized hiPSCs-CMs and CFs are generated for in vitro biological assessments.

It is proposed that the functionalities of developed micro-tissues will work in an in vivo model, such as in preclinical rodent model and eventually in clinical applications. This will improve myocardial function, vascular formation and integration of micro-tissues within the host myocardium. The utility of the injected micro-tissues in improving myocardial function can be evaluated, and vascular formation and integration of the micro-tissues with the host myocardium are investigated.

In one or more embodiments, functionalization of the surface of CMs with multipurpose GNWs are conjugated with cell adhesion promoting and vasculogenic peptides. Native ventricular myocardium consists of electrically conductive Purkinje fibers coupled with tightly packed cellular constructs consisting mainly of CMs and CFs. Previous work on the use of conductive nanomaterials (i.e. carbon nanotubes (CNTs), graphene oxide (GO), silicon (SO) nanowires, gold nanostructure) showed significant promise of these nanomaterials in enhanced functionalities of engineered cardiac tissues. However, most of these approaches relied on random dispersion of nanomaterials within scaffolding biomaterials (i.e. scaffoldbased approach) or cellular clusters without precise control over location or fate of the nanomaterials. Importantly, there are also potential cytotoxicity issues in the use of these nanomaterials (i.e. CNTs, GO, SO) for MRT. Nanoengineering is used to functionalize for the first time the surface of human induced pluripotent stem cell derived CMs (hiPSC-CMs), which will form the primary building blocks of the micro-tissues. For this, GNWs are used that are intrinsically electrically conductive, but in addition, the surface of GNWs are conjugated with cell adhesion-promoting RGD peptide (FIG. 1A). By providing nanoscale functionalization to promote cell-cell coupling (as a result of the presence of RGD peptide), as well as electromechanical integration with the surrounding host myocardium (as a result of the electrically conductive nature of GNWs) current limitations are addressed.

Neovascularization: Our approach is also designed to enhance neovascular formation by conjugation of vasculogenic VEGF-mimetic peptide (along with RGD), on the surface of GNWs. This strategy will address a significant limitation of current MRT approaches that lack vascular development to support and sustain implanted or injected engineered tissue constructs.

Scaffold-free cardiac micro-tissues with specific architectural arrangement: In our unique strategy, microscale technology (i.e. use of thermo-responsive microwells) is used to develop scaffold-free cardiac micro-tissues comprised of co-culture of functionalized hiPSC-CMs and CFs with specific architectural arrangement. In particular, CFs are arranged within the outer layer of the micro-tissues with the primary purpose of promoting the engraftment of the micro-tissues with the host upon injection through cell-ECM interaction and production of native ECM proteins (i.e. collagen) by CFs. Our approach is the first strategy to generate cardiac micro-tissues with this unique architectural arrangement. Native myocardium is a multi-cellular and adaptive tissue consisting of myocytes and non-myocyte cells.

The cellular mixture is significant as extensive studies show that the interaction between myocytes and non-myocytes, specifically CFs is an important component to maintain optimal functionalities of the myocardium through proper cellular signaling and gap junction proteins (i.e. Cx40, Cx43). Therefore, our unique strategy will lead to optimal functionalities of the microtissues through direct contact and paracrine CM-CF signaling. Although there may be resident CFs within the infarct zone thereby lessening the need for CFs in engineered micro-tissues, the majority of native CFs may be dysfunctional, are in activated pro-inflammatory state or already differentiated into myofibroblasts and may therefore not fully support the functionalities of injected CMs.

It is important to note that our previous body of work and expertise in developing viable, functional, synchronously contracting engineered cardiac tissue using GNWs embedded gelatin-based scaffold (FIGS. 2A-2E) and co-culture of CFs and CMs uniquely allow us to embark on this project and enhances its feasibility.

The embodiments herein develop this next generation of MRT, in totality, represents a conceptual and technological leap in innovation, rather than small incremental steps, from currently available technologies.

The embodiments herein develop scaffold-free, electrically conductive and vasculogenic cardiac micro-tissues comprised of hiPSCs-CMs and CFs. Efficient MRT of infarcted myocardium relies on critical factors including proper cell source, enhanced retention and cell-cell coupling and engraftment, electromechanical integration of the engineered tissues with the surrounding host myocardium and neovascularization. We generate scaffold-free, and electrically conductive cardiac micro-tissues comprised of co-culture of hiPSCs-CMs and CFs with specific architectural arrangement for MRT. We will utilize nanoscale technology to synthesize GNWs and conjugate them with RGD and VEGF-mimetic peptides. We will then use a microengineering approach to establish micro-tissues with hiPSCs-CMs functionalized with GNWs comprising the core and CFs comprising the outer layer (FIG. 1C). We will perform extensive in vitro characterization to assess maturity, cellular connectivity, and electrophysiological functionalities of the micro-tissues. Electrically conductive scaffold-free micro-tissues will have enhanced cell-cell coupling as well as optimal physiological functionalities (synchronous contractility) in vitro.

Figure 3:
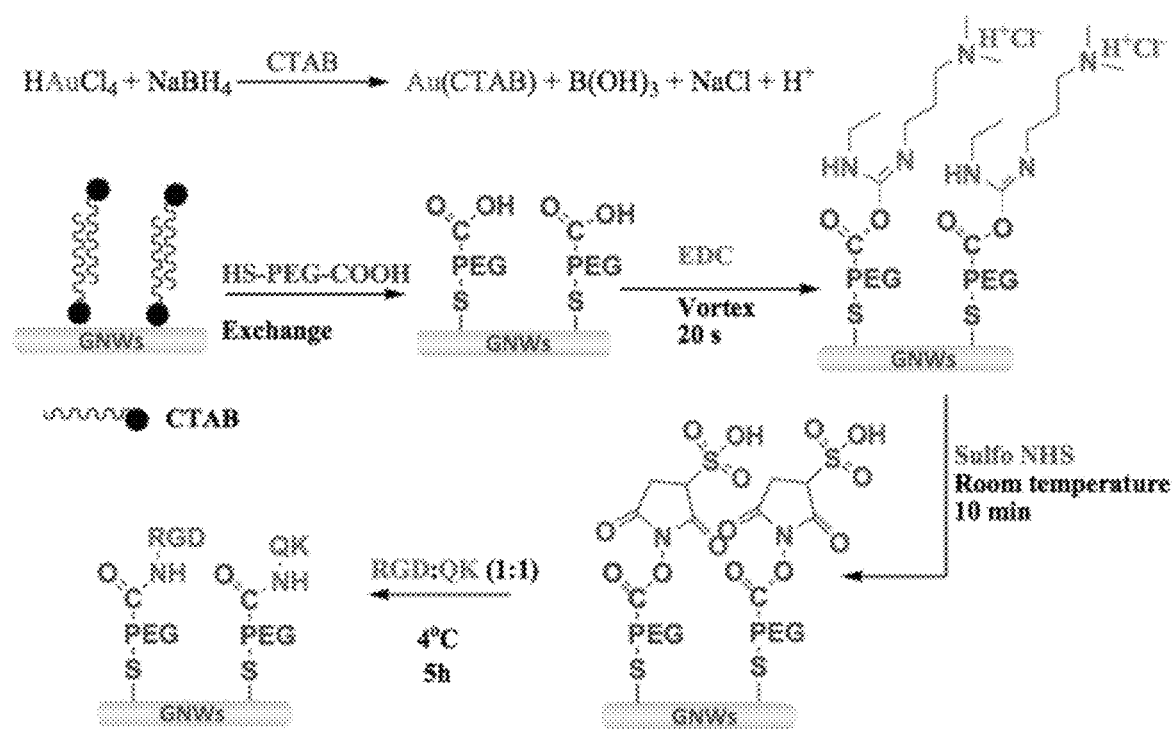
FIG. 3 illustrates a reaction synthetic scheme of GNW-PEGPeptide from GNW-CTAB via EDC/Sulfo NHS chemistry, in accordance with one or more embodiments.

The embodiments herein synthesize GNWs conjugated with RGD and VEGF-mimetic QK peptides GNWs, for example, with the average aspect ratio of 24 (~5 µm in length and ~50 nm in diameter) will be synthesized based on seed-mediated anisotropic growth method. We intend to start with 5 µm length for GNWs to reduce the likelihood of cellular uptake as previous studies have demonstrated the there is an inverse relation between the size and cellular uptake in gold nanomaterials. To conjugate RGD (cyclo (Arg-Gly-Asp-D-Phe-Cys) and VEGF-mimetic QK (Methacrylic acid-K(Ac)LTWQELYQLK(Ac)YK(Ac)GI-NH2 (SEQ ID NO: 1)) peptides on GNWs, first CTAB will be exchanged with COOH-PEGSH bi-linker; subsequently the peptides will be attached to the bi-linker via EDC/NHS procedure. The exchange of PEG bi-linker with CTAB will consist of two consecutive steps (FIG. 3). First, CTAB-capped GNWs will be centrifuged (2000 rpm, 20 min) two times and re-dispersed in 1 mM CTAB solution to reduce the concentration of CTAB to the critical micelle formation concentration (CMC in water for CTAB is ~1 mM).

After the second centrifugation/decantation, the supernatant will be discarded, and 400 µL of Tris buffer (50 mM, pH 3) will be added drop-wise to the GNWs pellet. To initiate the PEGylation process, 30 µL of COOH-PEG-SH (2 mM in DIW) will be added to the GNW-Tris mixture under vortexing and kept agitated for 1 min. The final mixture will be maintained undisturbed for 24 hr at room temperature to allow the completion of the PEGylation. The mixture will be then centrifuged (4000 rpm, 25 min) to remove the unreacted PEG bi-linkers, Tris buffer and free CTAB molecules. To further improve the CTAB-PEG bi-linker exchange, the freshly synthesized GNWPEG-COOH will be gently re-dispersed in 20% ethanol, followed by addition of 30 µL of COOH-PEG-SH (2 mM in 20% ethanol) to the mixture under gentle vortexing. The mixture will be kept undisturbed at room temperature for 24 hr. The two-step functionalized GNW-PEG-COOH will be harvested by centrifugation at 4000 rpm (25 min), and re-dispersed in 500 µL PBS.

To conjugate RGD and QK peptides, the carboxylic acid groups of GNW-PEG-COOH will be activated by adding EDC and Sulfo-NHS forming the corresponding GNW-PEG-COO—NHS ester. Briefly, GNW-PEGCOOH, dispersed in 500 μL PBS (obtained from the previous step) will be added with 2 mg of EDC, vortex for 20 sec and then 5.5 mg of Sulfo-NHS will be added to this solution at room temperature for 10 min.

Afterwards, 200 μL of 1:1 ratio of the peptides mixture (1 mg/mL in PBS each) will be added to the activated GNWs and the mixture will be kept in 4° C. for 5 hr. The GNW-PEG-RGD and GNW-PEG-QK mixture will be purified by centrifugation/decantation in PBS for 1 time. Upon preparation of GNWs and conjugation with RGD and VEGF-mimetic QK peptides, subsequent characterization will be performed using TEM, FTIR, Raman spectra and NMR. The presence and the size of GNWs will be obtained from TEM images. The conjugation of Au to the —SH group of HS-PEG-COOH will be characterized by the appearance of Au—S shift in Raman spectra. Furthermore, GNWs of the GNW-PEG-Peptides will be digested prior to taking NMR spectra. The appearance of amide I, amide II and amide A bands in the FTIR spectra and the appearance of the chemical shift corresponding to N—H bond in NMR spectra will confirm the presence and amount of peptides conjugated to GNWs.

One or more embodiments herein will generate scaffold-free cardiac micro-tissues, using GNW-functionalized hiPSCs-CMs and CFs, and generate micro-tissues comprised of hiPSCs-CMs and CFs. CFs will be transfected to stably express yellow fluorescent proteins (CF-YFP) for tracking within the micro-tissues, while enabling 3-color imaging. An initial co-culture ratio of 3:1 (hiPSCs-CMs:CFs) will be selected based on our previous studies to enhance tissue-level function.

Figure 4:
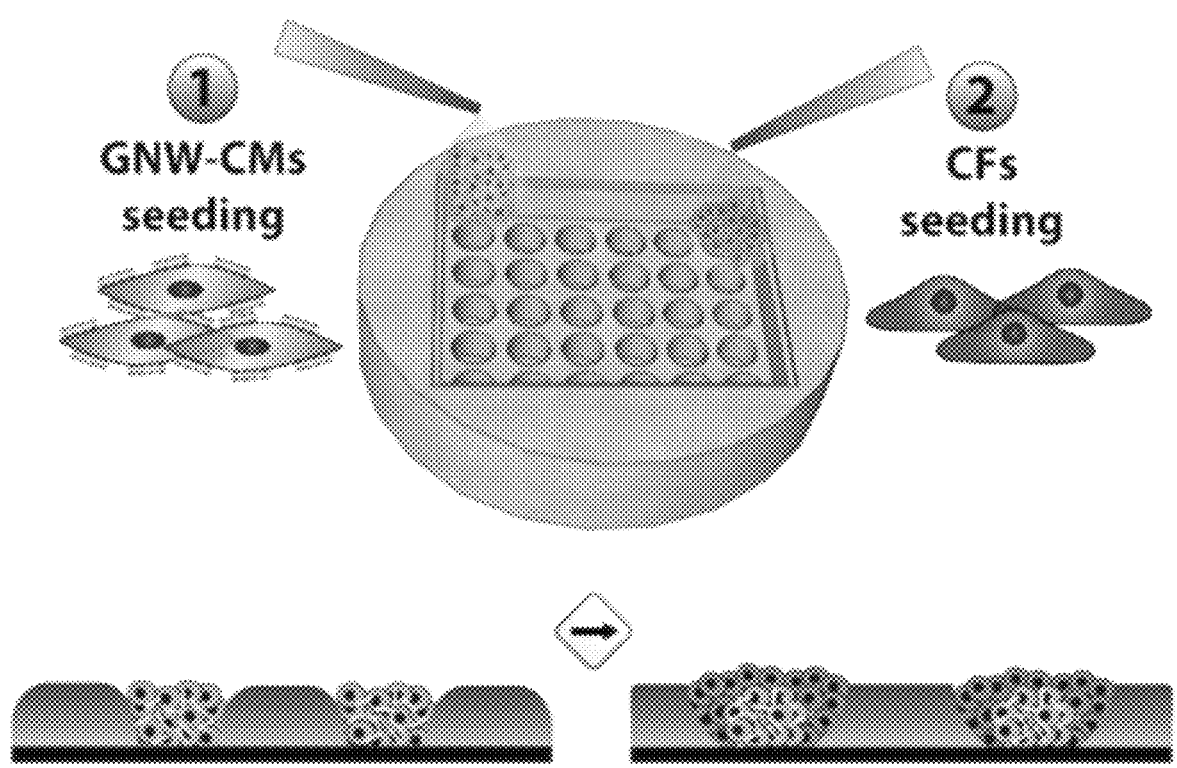
FIG. 4 illustrates a generation of scaffold-free microtissues comprised of co-culture of GNWs functionalized hiPSCs-CMs and CFs, in accordance with one or more embodiments.
Figure 5C:
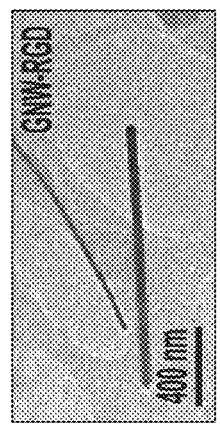
FIG. 5C illustrates a TEM micrograph of GNW-RGD, in accordance with one or more embodiments.
Figure 5B:
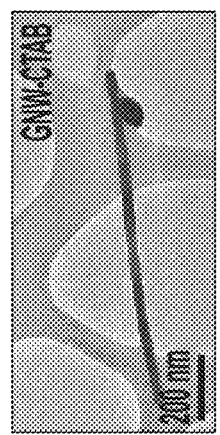
FIG. 5B illustrates a TEM micrograph of GNW-CTAB, in accordance with one or more embodiments.
Figure 5E:
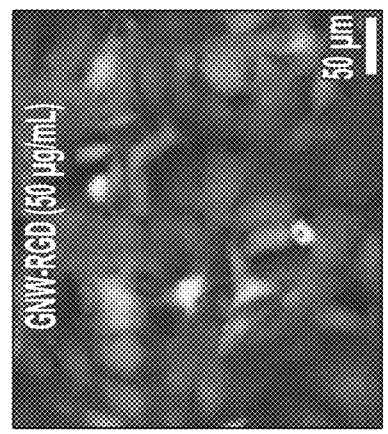
FIG. 5E illustrates viability results of GNW-RGD, in accordance with one or more embodiments.
Figure 5D:
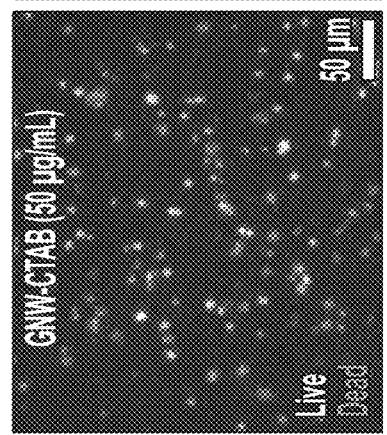
FIG. 5D illustrates viability results of GNW-CTAB, in accordance with one or more embodiments.
Figure 5A:
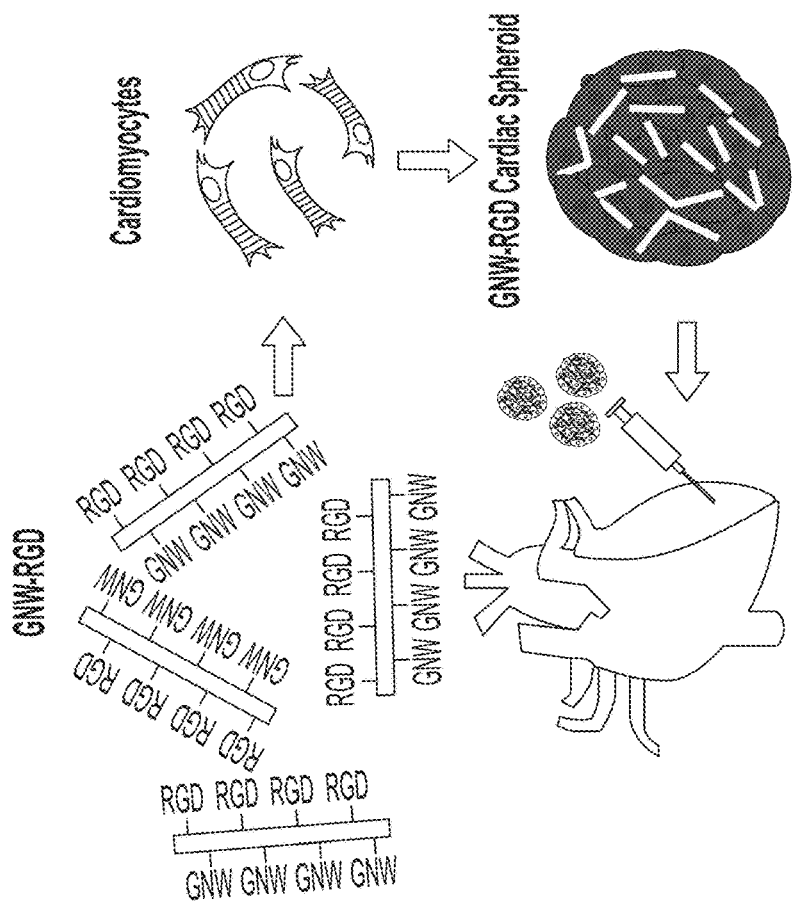
FIG. 5A illustrates a schematic diagram of the process of developing and implementing the GNW-RGD cardiac spheroid, in accordance with one or more embodiments.
Figure 5F:
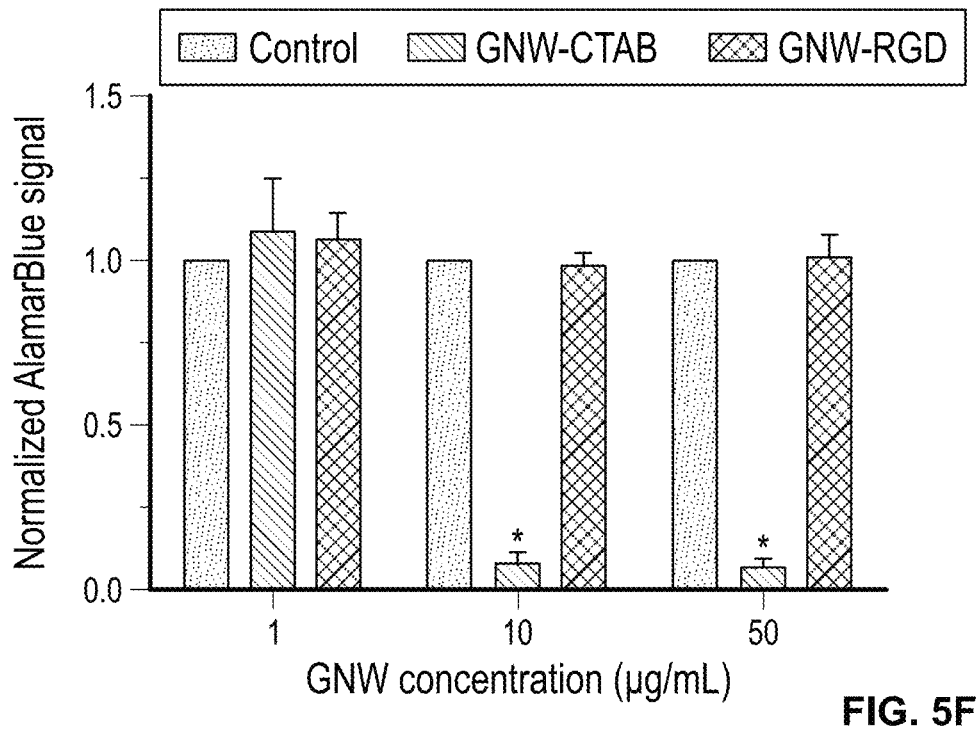
FIG. 5F illustrates normalized metabolic activity rate of cardiomyocytes, in accordance with one or more embodiments.
Figure 5G:
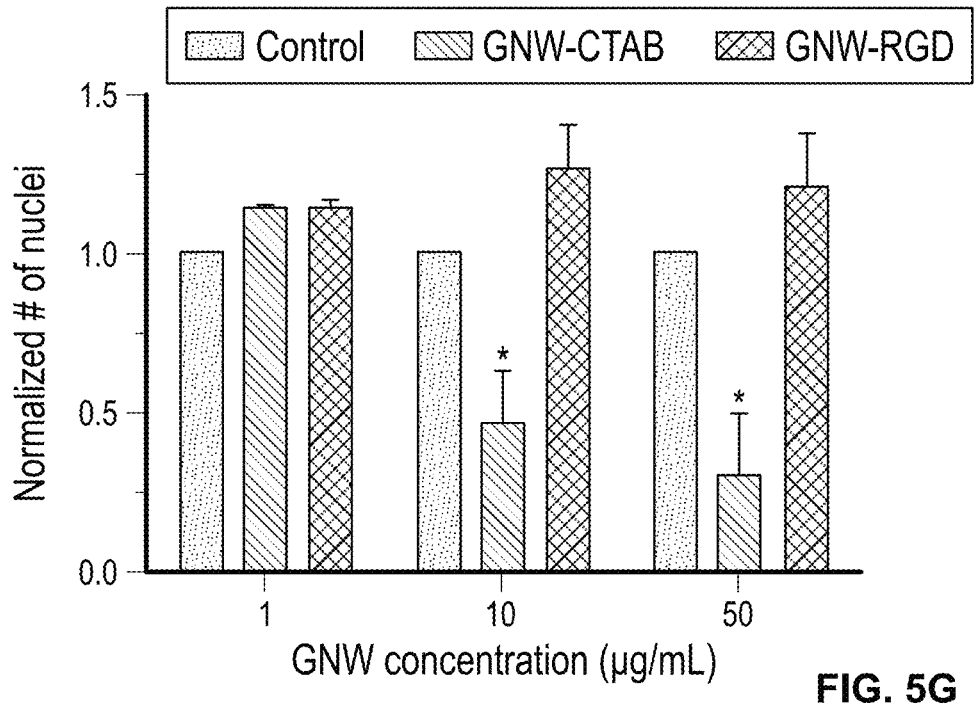
FIG. 5G illustrates a normalized number of nuclei per mm² showing cell retention on day of culture, in accordance with one or more embodiments.

To generate the micro-tissues, responsive PNIPAAam-based microwells (circular, starting with 250-300 μm diameter, 300 μm depth) along with twostep cell seeding process (hiPSCs-CMs followed by CFs, 3:1 ratio) (FIG. 3). Briefly, hiPSCs-CMs (10×106 cells/ml in culture media) will be mixed with different concentrations of functionalized GNWs (0, 2.5 and 5 μg/ml) and will be seeded on the microwells at 25° C. The microwells will be rinsed in PBS to remove excess cells. Subsequently, microwells will be placed inside 37° C. for 2 h to increase surface area and volume, opening up room for seeding CFs (FIG. 4). Upon sequential seeding of both cell types, microwells will be placed inside 37° C. for 7 days for the formation of final micro-tissues.

One or more embodiments include visualization of the GNWs on cell surface. For example, upon 1, 2, and 3 weeks, tissue sectioning and TEM imaging are utilized to investigate the localization of GNWs on cell membrane within the micro-tissues. Briefly, microtissues are fixed in 2.5% glutaraldehyde and post-fixed in osmium tetroxide (1%) with 1.5% K+ ferricyanide. Fixed samples will then be dehydrated in ethanol/propylene oxide and embedded in epoxy resin for sectioning. Ultrathin slices (100 nm, Ultra microtome) are prepared and stained using uranyl acetate and lead citrate.

In an example, assessment of cell-cell coupling within the micro-tissues is done as follows. On 1, 2, and 3 weeks of culture, the micro-tissues are fixed in 4% (v/v) paraformaldehyde (PF) in PBS and immunohistochemistry (IHC) consistent with our previous studies, will then be performed in each experimental condition (mono- and co-culture with defined concentrations of GNWs) to co-stain CX40, CX43 and CX45 gap junction proteins (Alexa Fluor 595, different samples) with sarcomeric proteins (MLC2a, MLC2v, α-actinin, α-MHC, Alexa Fluor 488). Within all the samples, the cells' nuclei will be stained with DAPI. The selection of secondary antibodies will enable 3-color imaging and identification of hiPSCs-CMs and YFP-CFs. We will quantify coverage area of the gap junction proteins within the selected regions of interest (ROIs, 300×300 μm2) as a function of GNWs concentrations, as well as the presence of CFs. Within different sets of samples we will use western blot to quantify the expression of gap junction proteins (CX40, CX43 and CX45). Briefly, micro-tissues in each experimental condition (mono- and co-culture with defined concentrations of GNWs) will be dissociated using AccuMax® solution (Innovative Cell Technologies). Cell suspension will be centrifuged at 1500 RPM for 5 min and supernatant removed. We will specifically look into the expression levels of CX40, CX43 and CX45. Extracted proteins will be ran through gel electrophoresis (SDS-PAGE). Proteins will be transferred to nitrocellulose membranes, and membranes treated with antibodies against corresponding cardiac markers and normalized against GAPDH. Densitometric analysis will be carried out with ImageJ software. In the co-culture condition, we will also assess the expression of secreted ECM proteins including laminin, fibronectin and collagen. Expected outcomes: Significantly higher area coverage and expression of gap junction proteins (Cx40/Cx43/Cx45) quantified by IHC and western blot in presence of GNWs and co-culture group with CFs.

Contractility of the micro-tissues and sarcomere organization: The spontaneous contractility of the microtissues are assessed using real time video microscopy and a custom MATLAB code to quantify beating frequency (beats per min, BPM) and contractile signal patterns of the cells upon 1, 2, and 3 weeks consistent with our publications (n=3). Side-by-side of contractility analysis, we will utilize IHC images to analyze for sarcomere organization within the selected regions of interest (ROIs, 300×300 μm2) within each condition. Consistent to our previous work, this analysis will determine whether conjugated GNWs impart a significant enhancement on contractility of the micro-tissues correlated to sarcomere organization. Enhanced contractility of the micro-tissues (i.e. spontaneous beating synchrony) is expected within different ROIs, in groups functionalized with GNWs. Significantly increased alignment index of sarcomeres positively correlated with beating synchrony of the micro-tissues.

Intracellular calcium (Ca2+) transients and electrophysiologic responsiveness of the micro-tissues: For Ca2+ transients measurements, samples will be exposed to 2.3 mM fluo-4 AM and 0.1% Pluronic F-127 for 15 min at 37° C. After 15 min, samples will be washed 3× in Tyrode's solution. Ca2+ transients will be imaged using confocal microscopy (63×) at 5-10 locations of each sample. Additionally, we will utilize qPCR analysis to assess upregulation of genes handling calcium proteins (i.e. SERCA2, RYR2, CACNAIC) in presence of GNWs. Within different samples, conduction velocity of cardiac micro-tissues will be analyzed using voltage sensitive dye RH-237. To determine contractile responsiveness to extraneous electrophysiologic signal (to mimic electrical signal from host myocardium), micro-tissues will be stimulated using platinum electrodes with 0.5-2 Hz, 5 V and 1-2 ms biphasic square pulses.

Subsequently, action potential (AP) will be measured (5-10 locations) and conduction velocity quantified. Expected outcomes: Synchronized calcium (Ca2+) transients spikes across multiple ROIs of the microtissues as well as increased upregulation of genes handling calcium proteins as function in groups conjugated with GNWs. Increased level of action potential in co-culture groups with conjugated GNWs.

Assessment of vascular formation: We utilized a microfluidic chip to assess utility of VEGF-mimetic QK peptide in promoting vascularization within 3D gelatin-based hydrogels. In brief, human umbilical vein endothelial cells (HUVECs, density: 15×106 cells/ml) were encapsulated within gelatin based hydrogel matrix (thiolated gelatin, Gel-S) conjugated with variable concentrations of QK mathacrylate peptide (sequence: KLTWQELYQLKYKGI-C(SEQ ID NO: 2), 0, 100, 150, 200 µg/mL). Our findings demonstrated that, in control condition (w/o QK), cells were randomly distributed throughout the matrix with disconnected and round morphologies. Alternatively, incorporation of QK peptide resulted in formation of robust, inter-connected vascular network with significantly increased average branch length, branch diameter and vascular network coverage. We will utilize a similar assay to encapsulate HUVECs along with micro-tissues (scaffold-free) within the microfluidic platform to assess the role of VEGF mimetic QK peptide, conjugated on GNWs, on vascular formation within the surrounding of the micro-tissues. Significant increase in ECs connectivity (network formation) and vascular area coverage toward the core of micro-tissues due to the presence of VEGF-mimetic QK peptide within the GNWs on the surface of hiPSCs-CMs. This will allow selection of optimal length and concentration of GNWs to proceed with in vivo studies.

In one or more embodiments, if cellular uptake of GNWs occurs, we will adjust our synthesis process to increase the length to 7-10 µm. In case of cellular contraction and decrease in the size of micro-tissues to 150 µm, we will increase the diameter of the microwells (~300-350 µm). In case, if we do not observe statistically significant difference in contractility or Ca2+ transients in presence of GNWs, we will optimize and increase the concentration in the range of 7.5 to 10 µg/ml.

Embodiments further optionally include evaluating the functionalities of the developed cardiac micro-tissues in vivo in a rodent model (Months 16-24). Injectable cardiac micro-tissues, developed herein, are envisioned to significantly promote MRT through enhanced cell-cell coupling, cell-matrix interaction, electrical engraftment with the host myocardium and nonvascular formation. Therefore, it is important to evaluate biological and physiological performance of the injectable micro-tissue in vivo. In this, we will use small animal model (rodent) to study whether the developed cardiac micro-tissues will lead to such improved biological and physiological functionalities.

The next generation of MRT is discussed herein, utilizing a multidisciplinary and state-of-the-art approach based on nanoengineered hiPSCs-CMs functionalized with multipurpose GNWs. The embodiments provide for the ultimate development of injectable micro-tissues with superior cell-cell coupling, engraftment, electromechanical integration and neovascularization leading to effective functional MTR.

Gold Nanostructures

The gold nanostructures can be selected to optimize the utility of the resulting microtissue. Accordingly, the nature of the gold nanostructures is not critical, provided the resulting scaffold-free micro tissue possesses the desired physical properties and biological function. For example, the gold nanostructures can be 1D structures such as a wires, rods, or spheres. Typically the gold nanowires will have a width of about 20 nm to about 50 nm and a length of up to about 5 µm. Gold nanorods will typically have a width of about 50 nm and a length of up to about 100 nm, about 200 nm or about 300 nm. Gold nanospheres will typically have a diameter of up to about 50 nm or up to about 100 nm.

The gold nanostructures can also include 2D structures such as nano-plates. Typically the gold nanoplates will be 2D sheets having dimensions up to about 250-500 nm×250-500 nm.

Linkers

Figure 6:
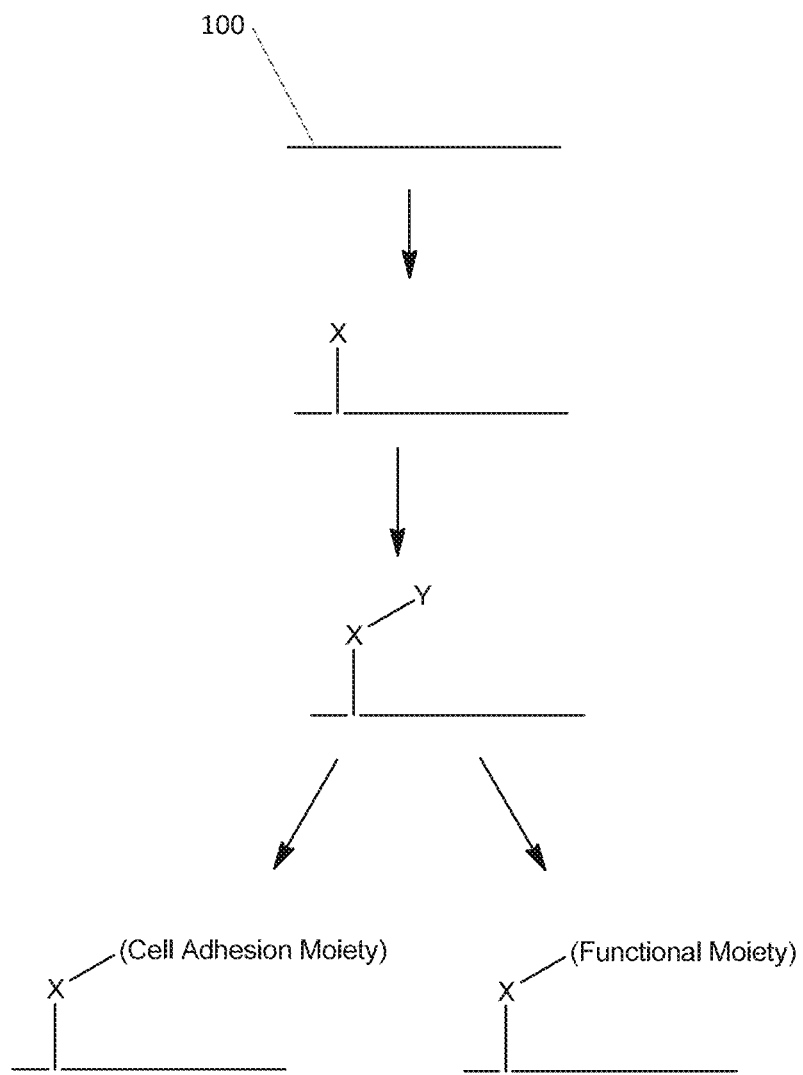
FIG. 6 illustrates a schematic diagram of decorated gold nanostructures and the preparation thereof, in accordance with one or more embodiments.

The gold nanostructures 100 can be linked to the cell-adhesion moiety or to the functional moiety through a direct chemical bond or through a linking group X, as shown in FIG. 6. In one embodiment of the invention the gold nanostructure is linked to the cell-adhesion moiety or to the functional moiety through a direct chemical bond. In another embodiment of the invention the gold nanostructure is linked to the cell-adhesion moiety or to the functional moiety through a linking group X. Any linking group that provides a GNW with desired properties and function may be used.

In one embodiment of the invention the linker has a molecular weight of from about 20 daltons to about 20,000 daltons.

In one embodiment of the invention the linker has a molecular weight of from about 20 daltons to about 5,000 daltons.

In one embodiment of the invention the linker has a molecular weight of from about 20 daltons to about 1,000 daltons.

In one embodiment of the invention the linker has a molecular weight of from about 20 daltons to about 200 daltons.

In another embodiment of the invention the linker has a length of about 5 angstroms to about 60 angstroms.

In another embodiment of the invention the linker separates the antigen from the remainder of the compound of formula I by about 5 angstroms to about 40 angstroms, inclusive, in length.

In another embodiment of the invention the linker is a divalent, branched or unbranched, saturated or unsaturated, hydrocarbon chain, having from 2 to 25 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy.

In another embodiment of the invention the linker is a divalent, branched or unbranched, saturated or unsaturated, hydrocarbon chain, having from 2 to 10 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy.

In another embodiment of the invention the linker is a divalent, branched or unbranched, saturated or unsaturated, hydrocarbon chain, having from 2 to 25 carbon atoms, wherein the chain is optionally substituted on carbon with one or more (e.g. 1, 2, 3, or 4) substituents selected from $(C_1-C_6)$alkoxy, $(C_3-C_6)$cycloalkyl, $(C_1-C_6)$alkanoyl, $(C_1$-

C$_6$)alkanoyloxy, (C$_1$-C$_6$)alkoxycarbonyl, (C$_1$-C$_6$)alkylthio, azido, cyano, nitro, halo, hydroxy, oxo (=O), carboxy, aryl, aryloxy, heteroaryl, and heteroaryloxy.

In another embodiment of the invention the linker is a divalent, branched or unbranched, saturated or unsaturated, hydrocarbon chain, having from 2 to 10 carbon atoms, wherein the chain is optionally substituted on carbon with one or more (e.g. 1, 2, 3, or 4) substituents selected from (C$_1$-C$_6$)alkoxy, (C$_3$-C$_6$)cycloalkyl, (C$_1$-C$_6$)alkanoyl, (C$_1$-C$_6$)alkanoyloxy, (C$_1$-C$_6$)alkoxycarbonyl, (C$_1$-C$_6$)alkylthio, azido, cyano, nitro, halo, hydroxy, oxo (=O), carboxy, aryl, aryloxy, heteroaryl, and heteroaryloxy.

In another embodiment of the invention the linker is a divalent, branched or unbranched, saturated or unsaturated, hydrocarbon chain, having from 2 to 10 carbon atoms.

In another embodiment of the invention the linker is a divalent, branched or unbranched, saturated hydrocarbon chain, having from 2 to 10 carbon atoms.

In another embodiment of the invention the linker is a divalent, unbranched, saturated hydrocarbon chain, having from 2 to 10 carbon atoms.

In another embodiment of the invention the linker is a divalent, unbranched, saturated hydrocarbon chain, having from 2 to 6 carbon atoms.

In another embodiment of the invention the linker is a divalent, unbranched, saturated hydrocarbon chain, having from 2 to 4 carbon atoms.

In another embodiment of the invention the linker comprises a polyethyleneoxy chain. In another embodiment of the invention the polyethyleneoxy chain comprises 2, 3, 4, 5, 6, 7, 8, 9, or 10 repeating ethyleneoxy units.

In another embodiment of the invention the linker is a divalent radical formed from a peptide.

In another embodiment of the invention the linker is a divalent radical formed from an amino acid.

In another embodiment of the invention the linker is a divalent radical of formula —S-(PEG)—C(=O)—, as illustrated in FIG. 3, wherein C(=O)— is bonded to the amino terminus of the RGD peptide. The molecular weight of PEG is 3500 Dalton g/mol.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenyl-alanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a (C$_1$-C$_6$)alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein). An amino acid can be linked to the remainder of a compound of formula I through the carboxy terminus, the amino terminus, or through any other convenient point of attachment, such as, for example, through the sulfur of cysteine.

The term "peptide" describes a sequence of 2 to 25 amino acids (e.g. as defined hereinabove) or peptidyl residues. The sequence may be linear or cyclic. For example, a cyclic peptide can be prepared or may result from the formation of disulfide bridges between two cysteine residues in a sequence. A peptide can be linked to the remainder of a compound of formula I through the carboxy terminus, the amino terminus, or through any other convenient point of attachment, such as, for example, through the sulfur of a cysteine. Preferably a peptide comprises 3 to 25, or 5 to 21 amino acids. Peptide derivatives can be prepared as disclosed in U.S. Pat. Nos. 4,612,302; 4,853,371; and 4,684,620, or as described in the Examples hereinbelow. Peptide sequences specifically recited herein are written with the amino terminus on the left and the carboxy terminus on the right.

Cell Adhesion Moiety

The gold nanostructures can be linked to one or more cell adhesion moieties. The cell adhesion moiety provides affinity for targeting of the gold nanostructures toward the cell membrane. Additionally, these cell adhesion moieties are envisioned to enhanced cell-cell coupling among cardiomyocytes as well as cell cell-matrix interaction and overall cellular retention between the micro-tissues and the surrounding host matrix upon implantation. In one embodiment of the invention, since we are targeting the affinity of the gold nanostructures toward the cell membrane and aim to enhance the cell-cell coupling as well as cell cell-matrix interactions, the cell adhesion moiety would be a peptide, which is conjugated to the surface of the gold nanostructures. In another embodiment of the invention the cell adhesion moiety is an integrin binding peptides such as RGD or DGEA (SEQ ID NO: 3) or other peptides GRGDSP (SEQ ID NO: 4) or GRGDY (SEQ ID NO: 5) peptides. These peptides belong to classes of synthetic peptides that contain the amino acids: specifically for RGD: Arg-Gly-Asp, for DGEA (Asp-Gly-Glu-Ala) (SEQ ID NO: 3), for GRGDSP (H-Gly-Arg-Gly-Asp-Ser-Pro-OH) (SEQ ID NO: 4) and for GRGDY (Gly-Arg-Gly-Asp-Tyr) (SEQ ID NO: 5). (See Tissue Eng. 2000 April; 6(2):85-103, Extracellular Matrix Cell Adhesion Peptides: Functional Applications in Orthopedic Materials. LeBaron RG1, Athanasiou KA. See also Cook, A. D., Hrkach, J. S., Gao, N. N., Johnson, I. M., Pajvani, U. B., Cannizzaro, S. M., and Langer, R. Characterization and development of RGD-peptide-modified poly (lactic acid-co-lysine) as an interactive, restorable biomaterial; J. Biomed. Mater. Res. 35, 13, 1997.) These peptides will mimic cellular attachment activity. (See Pierschbacher, M. D., and Ruoslahti, E. Cell attachment activity of fibronectin can be duplicated by small synthetic fragments of the molecule. Nature 309, 30, 1984. Pierschbacher, M. D., and Ruoslahti, E. Variants of the cell recognition site of fibronectin that retain attachment promoting activity. Proc. Natl. Acad. Sci. USA 81, 5985, 1984.) Other peptides can be used to promote cell adhesion through conjugation to the gold nanostructures.

Functional Moiety

The gold nanostructures can be linked to one or more functional moieties. The functional moiety provides for specific target functionalities such as promoting vascular formation toward the injected tissues, reduce inflammatory response upon injection of the cells or reduce apoptosis. In one embodiment of the invention the functional moiety is a peptide. The function moiety could also be aptamers (oligonucleotides)

In another embodiment of the invention the functional moiety is a vasculogenic peptide, an anti-inflammatory peptide, antiapoptotic/antinecrotic peptides. In one or more embodiments, the functional units and/or moieties includes one or more of vascularization peptides, anti-inflammatory peptides, antiapoptotic/antinecrotic peptides, or antioxidant peptides. For the vasculogenic peptides we can have: 1-QK (Methacrylic acid-K(Ac)LTWQELYQLK(Ac)YK(Ac)GI-NH2). (See Covalently immobilized VEGF-mimicking peptide with gelatin methacrylate enhances microvascularization of endothelial cells SP Parthiban, D Rana, E Jabbari, N Benkirane-Jessel, M Ramalingam Acta biomaterialia 51, 330-340). Or, VEGF memetic peptide [SLanc: K-(SL)3(RG)(SL)3-K-G-KLTWQE-LYQLKYKGI]. (See Vivek A. Kumar, Nichole L. Taylor, Siyu Shi, Benjamin K. Wang, Abhishek A. Jalan, Marci K. Kang, Navindee C. Wickremasinghe, Jeffrey D. Hartgerink. Highly Angiogenic Peptide Nanofibers. ACS Nano, 2015, 9(1), 860-868.)

Preparation of Modified Gold Nanostructures

The preparation of certain gold nanostructures that can be incorporated into the microtissues of the invention is illustrated in FIG. 6. For example, the gold nanostructure can be linked to a linking group (X), which can then be modified to incorporate an activating group (Y) that can be used to facilitate the attachment of the cell adhesion moiety or the functional moiety. Alternatively, the gold nanostructure can be linked directly to a group —X-Y in one step. Processes and reagents that can be used to modify a gold surface are known, for example, see Zhang, Z. & Lin, M. Fast loading of PEG-SH on CTAB-protected gold nanorods. *RSC Adv.* 4, 17760-17767 (2014), and/or Kinnear, C. et al. Gold Nanorods: Controlling Their Surface Chemistry and Complete Detoxification by a Two-Step Place Exchange. *Angew. Chem. Int. Ed.* 52, 1934-1938 (2013).

The linking group X can be attached to the gold nanostructure in any synthetically feasible linkage. In one embodiment, the gold surface can be attached to the linking group X through a covalent bond with a sulfur atom of X. The activating group Y can be a leaving group that can be displaced by an atom on the cell adhesion moiety or on the functional moiety—or the activating group Y can be a reactive group that can react with an atom on the cell adhesion moiety or on the functional moiety. In one embodiment, the activating group is sulfo N-hydroxysuccinamide (as illustrated in FIG. 3) or another activated group that is capable of forming an amide with an amine group of the cell adhesion moiety or on the functional moiety. Such activated amide forming groups and reaction conditions are known.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

---

What is claimed is:

1. A microtissue, comprising: one or more gold nanostructures linked to one or more cell adhesion peptides;
a plurality of cardiac myocytes or cardiac myoblasts, wherein the cardiac myocytes or cardiac myoblasts are conjugated to the one or more gold nanostructures, wherein the plurality of cardiac myocytes or cardiac myoblasts are arranged in a cluster; and
a plurality of fibroblasts, wherein the fibroblasts are arranged in at least one layer of fibroblasts that substantially surrounds the cluster of gold-nanostructure-conjugated cardiac myocytes or gold-nanostructureconjugated cardiac myoblasts, wherein optionally, the gold nanostructures are further linked to one or more anti-inflammatory peptides, one or more antiapoptotic peptides, one or more antinecrotic peptides, one or more antioxidant particles, one or more liposomes, one or more nanoliposomes, one or more microRNAs, or one or more siRNAs.

2. The microtissue of claim 1, wherein the one or more gold nanostructures are additionally linked to one or more anti-inflammatory peptides.

3. The microtissue of claim 1, wherein the cardiac myocytes are human-induced pluripotent-stem-cell-derived cardiac myocytes.

4. The microtissue of claim 3, wherein the one or more gold nanostructures are additionally linked to one or more vasculogenic peptides.

5. The microtissue of claim 4, wherein the one or more vasculogenic peptides comprises a VEGF-mimetic peptide.

6. The microtissue of claim 4, wherein the one or more vasculogenic peptides comprises a VEGF-mimetic QK-peptide.

7. The microtissue of claim 4, wherein the one or more cell adhesion peptides are RGD peptides.

8. The microtissue of claim 7, wherein the one or more gold nanostructures are capped with polyethylene glycol bi-linker.

9. The microtissue of claim 1, wherein the one or more gold nanostructures are wires, rods or plates.

10. A microtissue, comprising:
one or more gold nanostructures linked to one or more cell adhesion peptides;
a plurality of cardiac myocytes or cardiac myoblasts, wherein the cardiac myocytes or cardiac myoblasts are conjugated to the one or more gold nanostructures, wherein the plurality of cardiac myocytes or cardiac myoblasts are arranged in a cluster, and
a plurality of fibroblasts, wherein the fibroblasts are arranged in at least one layer of fibroblasts that substantially surrounds the cluster of gold-nanostructure-conjugated cardiac myocytes or gold-nanostructure-conjugated cardiac myoblasts, wherein the one or more gold nanostructures are coupled to a cell-targeting moiety.

11. The microtissue of claim 10, wherein the one or more gold nanostructures are linked to the cell-targeting moiety through a direct bond.

12. The microtissue of claim 10, wherein the one or more gold nanostructures are linked to the cell-targeting moiety through a linking group.

13. The microtissue of claim 12, wherein the targeting moiety is a RGD peptide including an amino terminus and the linking group is a divalent radical of formula —S-(PEG)—C(=O)—, wherein C(=O)— is bonded to the amino terminus and PEG is a polyethyleneoxy chain.

14. The microtissue of claim 12, wherein the linking group is a divalent, branched or unbranched, saturated or unsaturated, hydrocarbon chain, having from 2 to 25 carbon atoms, wherein one or more of the carbon atoms is optionally replaced by (O), and wherein the chain is optionally substituted on carbon with one or more substituents selected from (C1-C6)alkoxy, (C3-C6)cycloalkyl, (C1-C6)alkanoyl, (C1-C6)alkanoyloxy, (C1-C6)alkoxycarbonyl, (C1-C6)alkylthio, azido, cyano, nitro, halo, hydroxy, oxo (=O), carboxy, aryl, aryloxy, heteroaryl, and heteroaryloxy.

15. The microtissue of claim 10, wherein the cell adhesion moiety includes RGD, DGEA (SEQ ID NO: 3), GRGDSP (SEQ ID NO: 4), or GRGDY (SEQ ID NO: 5).

* * * * *